United States Patent
Kumar et al.

(10) Patent No.: US 12,403,070 B2
(45) Date of Patent: *Sep. 2, 2025

(54) INTRAVENOUS INFUSION DOSAGE FORM

(71) Applicant: Sun Pharmaceutical Industries Limited, Mumbai (IN)

(72) Inventors: Samarth Kumar, Baroda (IN); Prashant Kane, Baroda (IN); Subhas Balaram Bhowmick, Baroda (IN); Kirti Ganorkar, Maharashtra (IN); Nisarg Bipinchandra Mistry, Baroda (IN); Ramaji Karshanbhai Varu, Baroda (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 1320 days.

This patent is subject to a terminal disclaimer.

(21) Appl. No.: 16/952,565

(22) Filed: Nov. 19, 2020

(65) Prior Publication Data

US 2021/0128562 A1   May 6, 2021

Related U.S. Application Data

(63) Continuation of application No. 15/550,638, filed as application No. PCT/IN2016/050056 on Feb. 12, 2016, now Pat. No. 10,869,867.

(30) Foreign Application Priority Data

Feb. 13, 2015   (IN) .......................... 473/MUM/2015

(51) Int. Cl.
    *A61J 1/10*      (2006.01)
    *A61K 9/00*      (2006.01)
    (Continued)

(52) U.S. Cl.
    CPC ............... *A61J 1/10* (2013.01); *A61K 9/0019* (2013.01); *A61K 9/08* (2013.01); *A61K 31/519* (2013.01);
    (Continued)

(58) Field of Classification Search
    CPC .......... A61J 1/10; A61M 5/14; A61K 31/519; A61K 41/10; A61K 9/0019; A61K 9/18;
    (Continued)

(56) References Cited

U.S. PATENT DOCUMENTS

| | | | |
|---|---|---|---|
| 6,673,805 B2 * | 1/2004 | Lauria | A61P 35/00 |
| | | | 514/492 |
| 6,686,365 B2 * | 2/2004 | Riebesehl | A61K 45/06 |
| | | | 514/262.1 |

(Continued)

FOREIGN PATENT DOCUMENTS

| | | | | |
|---|---|---|---|---|
| EP | 2666463 A1 * | 11/2013 | ........... | A61K 31/519 |
| EP | 2992869 A1 | 3/2016 | | |

(Continued)

OTHER PUBLICATIONS

Indian Application No. 473/MUM/2015, Office Action mailed Feb. 28, 2020, 5 pages.

(Continued)

*Primary Examiner* — Philip R Wiest
(74) *Attorney, Agent, or Firm* — Blank Rome LLP

(57) ABSTRACT

The present invention refers to an intravenous infusion dosage form comprising a composition containing pemetrexed or its pharmaceutically acceptable salt, an osmagent and an aquous vehicle. The composition is present in a flexible infusion container containing an inert gas in the headspace. Additionally, a second container may be present surrounding the flexible infusion container.

16 Claims, 3 Drawing Sheets

(51) Int. Cl.
| | |
|---|---|
| *A61K 9/08* | (2006.01) |
| *A61K 31/519* | (2006.01) |
| *A61K 41/10* | (2020.01) |
| *A61K 47/02* | (2006.01) |
| *B65B 3/00* | (2006.01) |
| *B65B 7/02* | (2006.01) |
| *B65B 55/06* | (2006.01) |
| *A61M 5/14* | (2006.01) |

(52) U.S. Cl.
CPC .............. *A61K 41/10* (2020.01); *A61K 47/02* (2013.01); *B65B 3/003* (2013.01); *B65B 7/02* (2013.01); *B65B 55/06* (2013.01); *A61M 5/14* (2013.01)

(58) Field of Classification Search
CPC .......... A61K 47/02; B65B 3/003; B65B 7/02; B65B 55/06
See application file for complete search history.

(56) References Cited

U.S. PATENT DOCUMENTS

| | | | |
|---|---|---|---|
| 10,869,867 B2* | 12/2020 | Kumar | A61J 1/10 |
| 2009/0105684 A1* | 4/2009 | Balteau | A61J 1/1475 |
| | | | 604/415 |
| 2013/0231357 A1 | 9/2013 | Palepu et al. | |
| 2014/0296176 A1 | 10/2014 | Proia et al. | |
| 2014/0303254 A1 | 10/2014 | Hingorani et al. | |
| 2015/0045289 A1* | 2/2015 | West | A61J 1/10 |
| | | | 514/274 |
| 2015/0073000 A1* | 3/2015 | Khattar | A61K 31/519 |
| | | | 544/280 |
| 2015/0111905 A1* | 4/2015 | Khattar | A61K 47/18 |
| | | | 514/265.1 |
| 2016/0059597 A1 | 3/2016 | Suzuki | |

FOREIGN PATENT DOCUMENTS

| | | |
|---|---|---|
| JP | 2006111614 A | 4/2006 |
| JP | 2012188397 A | 10/2012 |
| JP | 2015127300 A | 7/2015 |
| WO | WO-2012121523 A2 | 9/2012 |
| WO | WO-2013144814 A1 | 10/2013 |
| WO | WO-2013165130 A1 | 11/2013 |
| WO | WO-2013179248 A1 | 12/2013 |
| WO | WO-2013179310 A1 | 12/2013 |
| WO | WO-2014182093 A1 | 11/2014 |
| WO | WO-2015092758 A1 | 6/2015 |
| WO | WO-2015145911 A1 | 10/2015 |

OTHER PUBLICATIONS

Japanese Application No. 2017-561054, Office Action mailed Jul. 7, 2020, 8 pages.

Zhang et al., Physical and chemical stability of pemetrexed in infusion solutions, Ann Pharmacother, Jun. 2006.

Yanping Zhang, et al., "Physical and Chemical Stability of Pemetrexed Solutions in Plastic Syringes", The Annals of Pharmacotherapy, Dec. 2005, pp. 2026-2028, vol. 39. 14.

Yanping Zhang, et al., "Physical and Chemical Stability of Pemetrexed in Infusion Solutions", The Annals of Pharmacotherapy, Jun. 2006, pp. 1082-1085, vol. 40.

International Search Report of PCT/IN2016/050056, dated May 31, 2016. [PCT/ISA/210].

Michalak, Olga , "Synthesis and Physiochemical Characterization of the Impurities of Pemetrexed Disodium, an Anticancer Drug", Molecules, 2015, 20:10004-10031.

Warner, Anne , "Development of a Purity Control Strategy for Pemetrexed Disodium and Validation of Associated Analytical Methodology", Journal of Pharmaceutical and Biochemical Analysis, 2015, 105:46-54.

* cited by examiner

INTRAVENOUS INFUSION DOSAGE FORM

FIELD OF THE INVENTION

The present invention relates to an intravenous infusion dosage form of pemetrexed or its pharmaceutically acceptable salt, having long term stability.

BACKGROUND OF THE INVENTION

Oxidation prone active ingredients are difficult to formulate as parenteral dosage forms, since the active agent degrades quickly in aqueous solutions due to presence of oxygen and water. Pemetrexed is one such oxidation prone active ingredient, which undergoes oxidation in the presence of oxygen and water to form degradative impurities. This leads to chemical degradation of the active drug moiety as well as physical discoloration of the solution, which makes the solution offensive and unmarketable. The currently available/marketed products of pemetrexed (for example Alimta®) are thus formulated as lyophilized powder which remains in a dry state until storage and needs to be reconstituted and diluted just before use. The lyophilized or freeze-dried preparations have considerable disadvantages. The process of preparing these lyophilisates is complicated and costly and reconstitution requires additional working steps which pose undesirable risks of personnel involved. Attempts have been made to prepare solutions of pemetrexed and stabilize the solutions by use of antioxidants, complexing agents like cyclodextrins, amino acids and other stabilizing agents. These excipients including antioxidants, amino acids, complexing agents etc. qualify as extraneous agents in the formulation of any pharmaceutical composition. The health authorities all over the world are very concerned about the level of such extraneous agents in the pharmaceutical compositions, particularly those meant for parenteral use. It is all the more desirable to avoid these agents for compositions comprising anti-neoplastic drugs like pemetrexed, since patient undergoing chemotherapy who are already facing severe side effects of the anti-neoplastic drug, cannot tolerate even a slight increase in the side effect which these extraneous agents may cause. It is thus desirable to keep the amount of excipients to a minimum. Thus, there is a need to develop a stable intravenous infusion dosage form of pemetrexed comprising a solution composition which do not use any extraneous agents such as antioxidants/amino acids/complexing agents etc. but is still stable for prolonged period of time, until the shelf life. The present invention fulfils this need.

SUMMARY OF THE INVENTION

The present invention provides an intravenous infusion dosage form comprising
a) a composition consisting essentially of pemetrexed or its pharmaceutically acceptable salt present at a concentration ranging from about 0.7 mg/ml to about 21 mg/ml, an osmogent and an inert gas in solution in a parenteral aqueous vehicle, the solution having a volume ranging from about 50 ml to 1000 ml,
b) a flexible infusion container containing the composition of (a) and an inert gas in the headspace,
c) a second container surrounding the flexible infusion container with an inert gas or vacuum in the space between the flexible infusion container and the second container,
wherein the total impurities are less than 2.0% by weight.

The present invention further provides an intravenous infusion dosage form comprising:
a) a composition consisting essentially of pemetrexed or its pharmaceutically acceptable salt present at a concentration ranging from about 0.7 mg/ml to about 21 mg/ml, an osmogent and an inert gas in solution in a parenteral aqueous vehicle, the solution having a volume ranging from about 50 ml to 1000 ml,
b) an infusion container containing the composition of (a) and an inert gas in the headspace,
c) optionally a second container surrounding the infusion container,
wherein the dosage form is subjected to moist heat sterilization, and wherein the total impurities are less than 2.0% by weight.

DETAILED DESCRIPTION OF THE INVENTION

Figure 1:
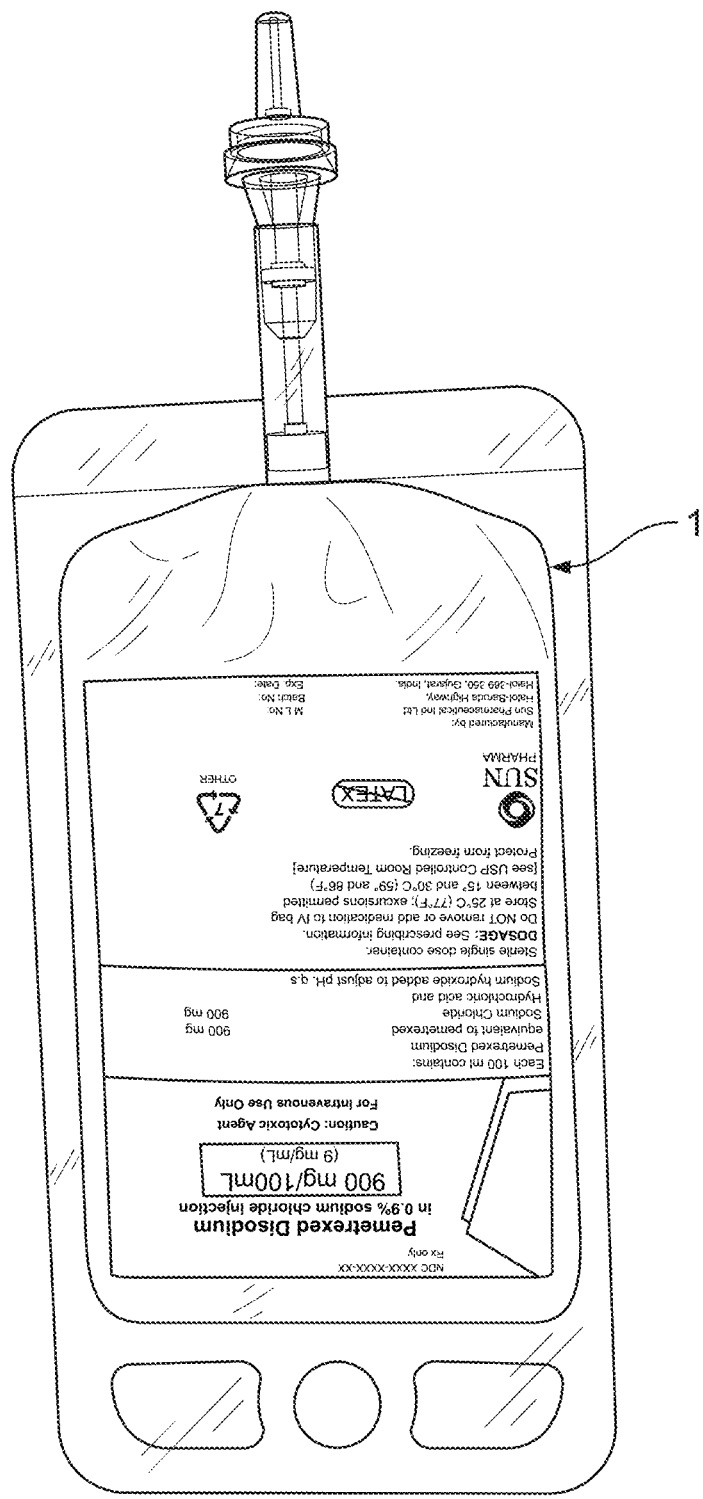
FIG. 1 illustrates one embodiment of the present invention wherein 1 represents a flexible infusion container.
Figure 2:
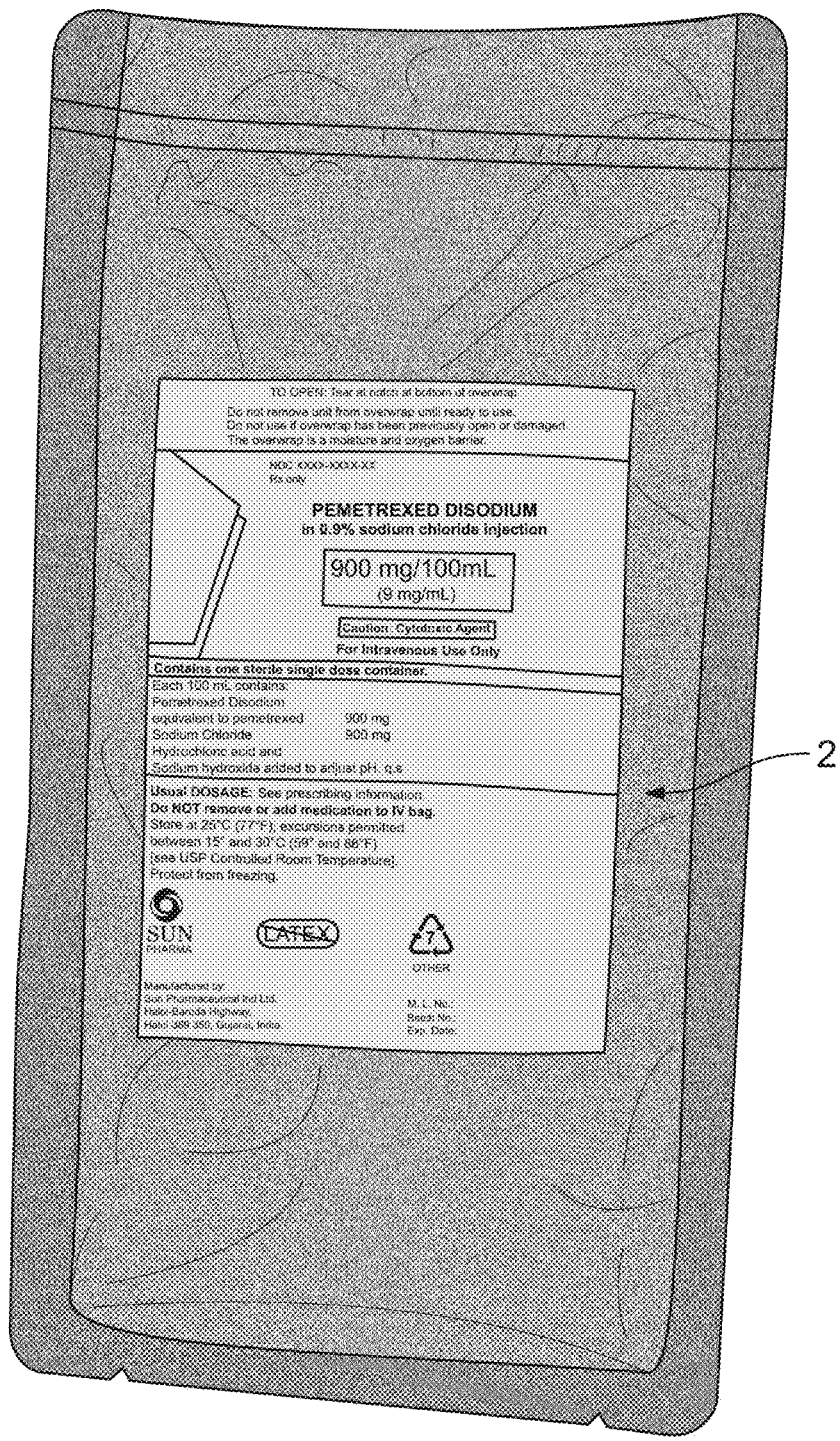
FIG. 2 represents the second container (2) made up of aluminum, which surrounds the infusion container.
Figure 3:
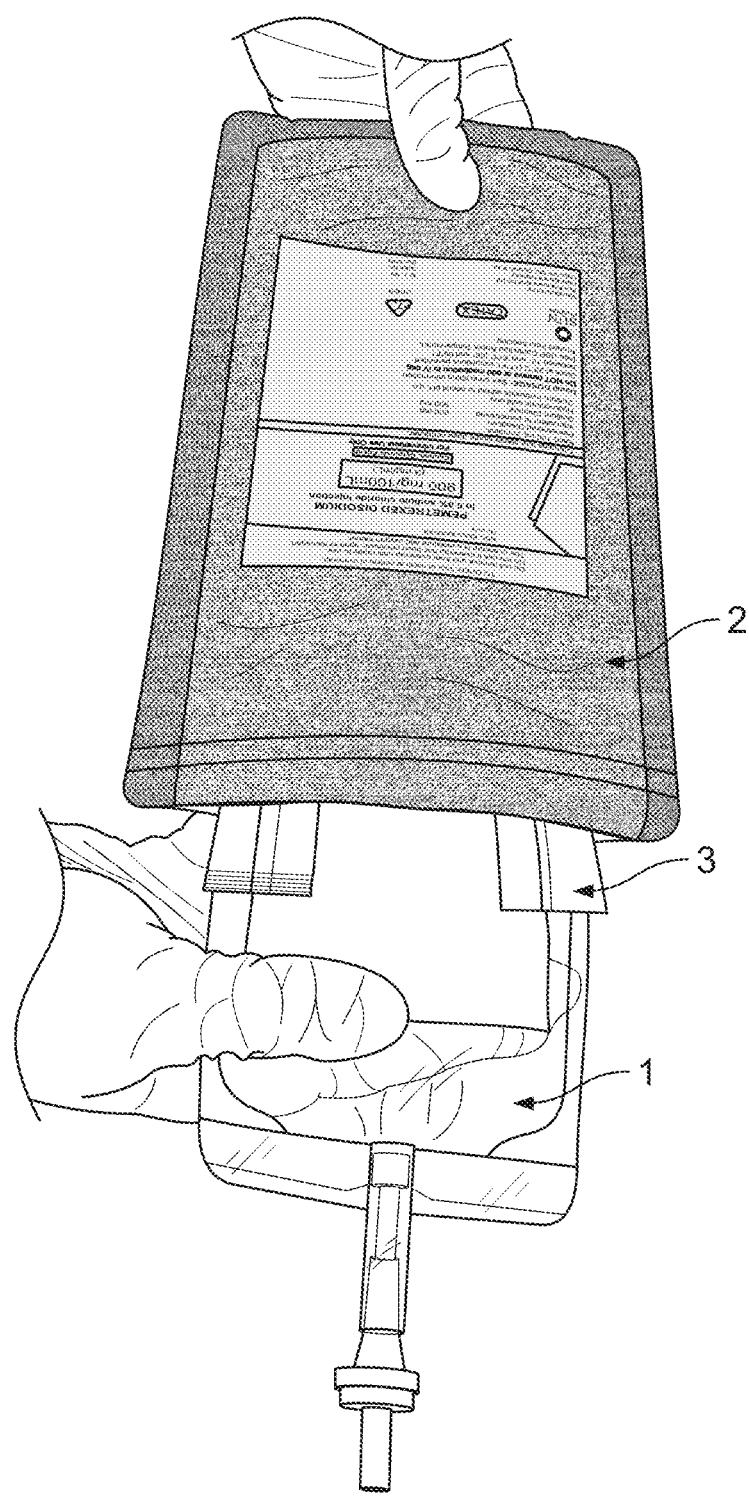
FIG. 3 represents the configuration of the intravenous infusion dosage form according to one embodiment of the present invention, wherein 1 is the flexible infusion container containing the composition of pemetrexed, 2 is the second container and 3 is the oxygen scavenger placed in the space between the infusion container and the second container.

The term "consisting essentially of" as used herein means that the composition of pemetrexed or its pharmaceutically acceptable salt is free of antioxidants, amino acids, amines, complexing agents, cyclodextrins or co-solvents such as propylene glycol or any other excipient that may act as a stabilizer for prevention of oxidative degradation of pemetrexed or its pharmaceutically acceptable salt. For instance, intravenous infusion dosage form according to the present invention is free of—antioxidants such as for example ascorbic acid, lipoic acid, propyl gallate, sulphur containing antioxidants such as sodium sulfite, sodium bisulfite, sodium metabisulfite, thioglycerol etc.; amino acids or amines such as cysteine, lysine, methionine, diethanolamine, tromethamine, meglumine etc; complexing agents such as cyclodextrins or other complexing agents; co-solvents such as for example ethanol, propanol; glycols like propylene glycol, polyethylene glycol, trimethylene glycol, butylene glycol etc.

The term 'antioxidant' as used in the context of the present invention refers to compounds possessing higher oxidation potential than pemetrexed. For the purpose of clarity, the term "antioxidant" as used herein is not intended to include chelating agents. Suitably, the intravenous infusion dosage form is free of antioxidants such as ascorbic acid, lipoic acid, propyl gallate, sulphur containing antioxidants such as sodium sulfite, sodium bisulfite, sodium metabisulfite, thioglycerol and the like.

The term 'total impurities' as used herein refers to summation of all known and unknown impurities of pemetrexed or its pharmaceutically acceptable salt present in the composition of the present invention, either initially or upon storage. The total impurities are expressed as % by weight i.e. % of the labeled pemetrexed content of the composition. By the phrase total impurities less than 2% by weight, it may be understood that the intravenous dosage form contains total impurities below 2% by weight of pemetrexed at any given point in time during the shelf life of the product, at room temperature (15-30° C.). The assay of drug as well as contents of known and unknown impurities may be analyzed by any suitable means. In one specific method, it was analyzed by high performance liquid chromatography method. Any suitable chromatographic technique may however be used.

Impurity B, as used herein in the specification is a degradation impurity of pemetrexed and is chemically named as (2S,2'S)-2,2'-[[(5R)-2,2'-diamino-4,4',6-trioxo-1,4,4',6,7,7'-hexahydro-1'H,5H-5,6'-bipryrolo[2,3-d]pyrimidine-5,5'-diyl]bis(ethylene benzene-4,1-diylcarbonylimino)]dipentanedioic acid. The chemical structure of impurity B is as follows:

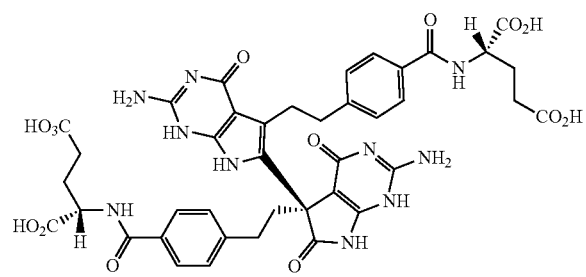

Impurity C, as used herein in the specification is another degradative impurity of pemetrexed and is chemically named as (2S,2'S)-2,2'-[[(5S)-2,2'-diamino-4,4',6-trioxo-1,4,4',6,7,7'-hexahydro-1'H,5H-5,6'-bipyrrolo[2,3-d]pyrimidine-5,5'-diyl]bis(ethylenebenzene-4,1-diylcarbonylimino)] dipentanedioic acid. The chemical structure of impurity C is as follows:

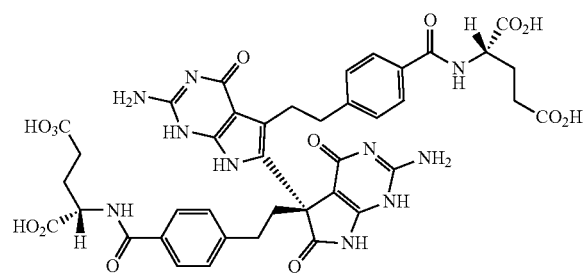

The term "sterile" as used in the context of the invention, means that the aqueous solution has been brought to a state of sterility and the solution complies with the sterility requirements of the standard Pharmacopoeias like United States Pharmacopoeias (USP) until the shelf life.

According to one aspect of the invention, there is provided an intravenous infusion dosage form comprising:
a. a composition consisting essentially of pemetrexed or its pharmaceutically acceptable salt present at a concentration ranging from about 0.7 mg/ml to about 21 mg/ml, an osmogent and an inert gas in solution in a parenteral aqueous vehicle, the solution having a volume ranging from about 50 ml to 1000 ml,
b. a flexible infusion container containing the composition of (a) and an inert gas in the headspace,
c. a second container surrounding the flexible infusion container with an inert gas or vacuum in the space between the flexible infusion container and the second container, wherein the total impurities are less than 2.0% by weight.

According to another aspect, there is provided an intravenous infusion dosage form comprising:
a. a composition consisting essentially of pemetrexed or its pharmaceutically acceptable salt present at a concentration ranging from about 0.7 mg/ml to about 21 mg/ml, an osmogent and an inert gas in solution in a parenteral aqueous vehicle, the solution having a volume ranging from about 50 ml to 1000 ml,
b. an infusion container containing the composition of (a) and an inert gas in the headspace,
c. optionally a second container surrounding the infusion container,
wherein the dosage form is subjected to moist heat sterilization, and wherein the total impurities are less than 2.0% by weight.

According to another aspect, there is provided an intravenous infusion dosage form comprising:
a. a composition consisting essentially of pemetrexed or its pharmaceutically acceptable salt present at a concentration ranging from about 0.7 mg/ml to about 21 mg/ml, an osmogent and an inert gas in solution in a parenteral aqueous vehicle, the solution having a volume ranging from about 50 ml to 1000 ml,
b. an infusion container containing the composition of (a) and an inert gas in the headspace,
c. a second container surrounding the flexible infusion container with an inert gas or vacuum in the space between the flexible infusion container and the second container
wherein the dosage form is subjected to moist heat sterilization and wherein the total impurities are less than 2.0% by weight.

In one embodiment, the composition comprises pemetrexed or its pharmaceutically acceptable salt. The suitable pharmaceutically acceptable salts of pemetrexed base, include, but are not limited to, ammonium, and substituted ammonium salts, such as for example, the sodium, potassium, lithium, calcium, magnesium, aluminum, zinc, ammonium, trimethylammonium, triethyl ammonium, monoethanolammonium, triethanol ammonium, tromethamine, pyridinium, substituted pyridinium, and the like. Although, any suitable pharmaceutically acceptable salts of pemetrexed may be used, preferably, the pharmaceutically acceptable salt is pemetrexed disodium heptahydrate. The amount or concentration of pemetrexed used in the present disclosure is expressed as amounts equivalent to pemetrexed free acid form.

Pemetrexed or its pharmaceutically acceptable salt is present in the composition of the intravenous dosage form of the present invention in amounts ranging from about 0.01 mg/ml to about 30 mg/ml, such as 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 6, 7, 8, 9, 10, 11, 12, 13, 14, 15, 16, 17, 18, 19 or 20 mg/ml, for example in an amount ranging from about 0.7 mg/ml to about 21 mg/ml. In one embodiment, pemetrexed disodium heptahydrate is used and it is present in an amount ranging from 0.7 mg to 21 mg/ml, such as, 5 mg/ml to 15 mg/ml, for example 9 mg/ml (expressed as amount equivalent to pemetrexed free acid form).

In one embodiment, the composition comprises pemetrexed or its pharmaceutically acceptable salt present at a concentration ranging from about 0.7 mg/ml to about 21 mg/ml. In one embodiment the intravenous infusion dosage form comprises an infusion container.

The composition of pemetrexed present in the infusion container consists essentially of pemetrexed or its pharmaceutically acceptable salt, an osmogent and an inert gas dissolved in a parenterally acceptable vehicle. In one embodiment the composition comprises an osmogent. In one embodiment the composition comprises an inert gas.

In one embodiment, the parenterally acceptable aqueous vehicle is water for injection or any other aqueous vehicle suitable for parenteral administration. In one embodiment the composition has a volume in the range of about 50 to 1000 ml. The volume of the composition contained in the infusion container may range from about 50 ml to about 1000 ml, such as 55, 60, 65, 70, 75, 80, 85, 90, 95, 100, 150, 200, 250, 300, 350, 400, 450, 500, 600, 700, 800 or 900 ml, for example, from about 75 ml to about 500 ml. In one particular embodiment, the volume of composition is 100 ml. The intravenous dosage form of the present invention has such configuration which makes the dosage form suitable for directly infusing or may also be referred to as 'ready-to administer- or ready to infuse dosage form. The dosage form has a particular concentration and volume of the composition in each container, such that there is no requirement of dilution before administration i.e. the composition can be directly infused from the infusion container to the patient in need thereof. Such dosage forms of pemetrexed are particularly advantageus in that they do not require any intermediate steps of dilution or reconstitution before administration of the intravenous infusion to the patient.

In a particular embodiment, the concentration of pemetrexed or its pharmaceutically acceptable salt may vary from about 0.7 mg/ml to about 21 mg/ml and wherein the volume of drug solution per unit dosage form may range from about 50 ml to about 1000 ml. The concentration and volume of the solution are tailored to achieve desired dose of pemetrexed. It is preferable that concentration and volume is such that for patient with an average body surface area (BSA), only one unit of the dosage form is sufficient to deliver the prescribed dose. For instance, for a patient having a BSA of 1.6 mg/m$^2$ the total dose in mg, based on approved dose of 500 mg/m$^2$ comes to be 800 mg. In one embodiment, the intravenous infusion dosage form of the present invention comprises 100 ml of pemetrexed solution having a concentration of 8 mg/ml. In another embodiment, the concentration of pemetrexed or its pharmaceutically acceptable salt may vary from about 5.0 mg/ml to about 15 mg/ml and wherein the volume of drug solution per unit dosage form may range from about 50 ml to about 1000 ml. The concentration and volume of the solution are tailored to achieve the desired dose of pemetrexed.

The composition which is in the form of an aqueous solution comprises an osmogent, a parenterally acceptable aqueous solvent, and if required a pH adjusting agent. In one embodiment the composition comprises an osmogent. The osmogent is an agent used to make the composition or solution of pemetrexed isosmotic or isotonic to the plasma fluids, such that the composition/solution has an osmolality in the range of about 250-375 mOsm/kg, preferably 270-330 mOsm/kg. The osmogent may be used in suitable amounts to make the composition isotonic having an osmolality in the above range. The osmogent used in the composition of the present invention may be selected from, but not limited to, sodium chloride, potassium chloride, calcium chloride, mannitol, sorbitol, dextrose, sucrose and the like and mixtures thereof. According to one preferred embodiment, the osmogent is sodium chloride. It may be used in an amount ranging from about 0.4% w/v to about 1.0% w/v. According to another embodiment, the osmotic agent may be dextrose and it may be used in an amount ranging from about 2% w/v to about 5.0% w/v.

In one embodiment, the composition of pemetrexed comprises a pH adjusting agent. The use of a pH adjusting agent is optional. It may be suitably used, if needed, to maintain the pH of the solution composition in the range of about 6.0 to 9.0, preferably from about 7.0 to 8.0, more preferably from about 7.0 to 7.4. The solution may have a pH in the desired range even without adding a pH adjusting agent under the effect of other ingredients present in the solution. The pH adjusting agent that may be used in the composition of the present invention includes, but are not limited to, sodium hydroxide, hydrochloric acid, sulfuric acid, acetic acid, tartaric acid, potassium hydroxide and the like and mixtures thereof.

The composition of the present invention is in the form of an aqueous solution. The aqueous solution contains an inert gas in the dissolved state. The inert gas in one embodiment may be nitrogen, argon or helium or mixtures thereof. The inert gas in the dissolved state in solution may be achieved by suitable means like purging of the inert gas in solution. Purging of inert gas may be carried out at one or more stages while manufacturing the composition or bulk solution of pemetrexed. This may include inert gas purging of the aqueous parenteral vehicle like water for injection before the addition of pemetrexed, and purging of the aqueous solution during or after the addition of pemetrexed or other excipient(s). The solution composition of pemetrexed according to one preferred embodiment of the present invention consists essentially of an inert gas in the solution, such that the content of dissolved oxygen in the solution having parenteral aqueous vehicle is less than 2 ppm (parts per million), preferably less than 1 ppm.

The infusion container of the present invention which contains the composition of pemetrexed, may be flexible or rigid in nature. The infusion container is preferably a single compartment container, suitable for parenteral infusion of the composition container therein. The container may be single layered or multi layered. In one embodiment, the perfusion containers have a single outlet meant for withdrawal of the aqueous solution from the container while being administered.

In one embodiment, the intravenous infusion dosage form of the present invention comprises a flexible infusion container which is made up of a plastic material or other polymeric material. Non limiting examples of the flexible infusion container include an infusion hag, a flexible infusion pouch, a soft bag, an infusion bottle, a film, or a plastic pre-filled syringe. The plastic or any other polymeric material of which the flexible infusion container is made, may be selected from, but not limited to, polyolefin polymers-polyethylene, polypropylene; cyclo olefin polymers, cyclo olefin copolymers, polypropylene based polyolefin polymers; polyamides, polyesters, ethylene vinyl acetate, modified polyolefin-polyethylene polymers or styrene-polyolefin based polymers and block co-polymers thereof. These flexible infusion containers may have one or more layers of plastic/polymeric materials.

In preferred embodiments, the plastic or polymeric material which constitute the flexible infusion container have an oxygen transmission rate of about 100 to 1400 (ml or cm$^3$)/(m$^2$·24 hour·atm), a water vapour transmission rate of about 0.2 to 6.0 g/(m$^2$·day) and a carbon dioxide transmission rate of about 3000 to 6500 (ml or cm$^3$)/(m$^2$·24 hour·atm). In one specific embodiment, the flexible infusion container is made up of an outer layer of polyamide 11, a middle tie of modified polyolefin and an inner layer of linear low density polyethylene. These containers have a water vapour transmission rate of 2 g (m²·day) when measured at (40° C./90% relative humidity); oxygen transmission rate of 900 ml/(m²·24 hour·atm) when measured at (23° C./0% relative humidity) and carbon dioxide transmission rate of 600 ml/(m²·24 hour·atm) when measured at 23° C./0% relative humidity. Such containers are available commercially and are manufactured by Hosokawa as Polyelite AE-1®. In another embodiment, the flexible infusion container is made up of a material comprising a polymer of cyclic olefin such as cyclooolefin homopolymer or cycloolefin copolymer or mixture thereof. Specifically, in a particular embodiment, the flexible infusion container comprises an inner layer made up of a cycloolefin polymer, a middle layer made up of linear low density polyethylene polymer and an outer layer made up of low density polyethylene polymer. The inner layer remains in contact with the composition. Such containers are available commercially and are manufactured by Hosokawa as Polyelite EHC® film bag. These containers have a water vapour transmission rate of 2 g (m²·day) when measured at (40° C./90% relative humidity); oxygen transmission rate of 570 ml/(m²·24 hour·atm) when measured at (23° C./0% relative humidity) and carbon dioxide transmission rate of 3400 ml/(m²·24 hour·atm) when measured at 23° C./0% relative humidity. In another embodiment, the flexible infusion container is made up of an outer layer of polypropylene polymer with styrene-ethylene-butylene (SEB) block copolymer and a middle and inner layer made up of polypropylene based polyolefin polymer with styrene-ethylene butylene block copolymer. Such containers are available commercially under the brand name Inerta 103® and are manufactured by Technoflex. These containers have a water vapour transmission rate of 0.62 g (m²·day) when measured at 23° C./60% relative humidity; oxygen permeability of 1110 ml/(m²·24 hour·atm) when measured at 23° C./40% relative humidity and carbon dioxide transmission rate of 5149 ml/(m²·24 hour·atm). In another embodiment, the flexible container is made up of multilayer polyolefin film having layers from outside to inside made up of CPET-Tie-PE-Tie-EPC. Such containers are available as M312 and M312A® films by Sealer Air Corporation. These containers have a water vapour transmission rate of 5.0 g (m²·day) when measured at 38° C./100% relative humidity; oxygen transmission rate of 1315 cm³/(m²·24 hour·atm) when measured at 73° F./0% relative humidity and carbon dioxide transmission rate of 3945 cm³/(m²·24 hour·atm).

In one specific embodiment, the flexible infusion containers, particularly an infusion bag, may include a Minitulipe® infusion port which is an infusion connector having three assembled parts including a central stopper made up of chlorobutyl rubber (latex free); an upper breakable part and a bottom part, both made up of polycarbonate. In one embodiment, the flexible infusion container contains a delivery port end for insertion of an infusion set cannula/needle. In one embodiment, the flexible infusion container/bag and the delivery port connecting to the infusion needle form a system whereby during administration of the solution to the patient the vacuum created by outgress of solution is accommodated by the elasticity or flexibility of the infusion bag instead of ingress of external non-sterile air. The dosage form can advantageously maintain the sterility of the solution until it reaches the patient.

Further it was found that when the infusion container is a rigid container, the intravenous dosage form remained stable without the presence of second container. Accordingly, in one aspect, the present invention provides an intravenous infusion dosage form comprising
(a) a composition consisting essentially of pemetrexed or its pharmaceutically acceptable salt present at a concentration ranging from about 0.7 mg/ml to about 21 mg/ml, an osmogent and an inert gas in solution in a parenteral aqueous vehicle, the solution having a volume ranging from about 50 ml to 1000 ml,
(b) a rigid infusion container containing the composition of (a) and an inert gas in the headspace,
(c) optionally, a second container surrounding the infusion container.

wherein the total impurities are less than 2.0% by weight.

In yet another aspect, the present invention provides an intravenous infusion dosage form comprising
(a) a composition consisting essentially of pemetrexed or its pharmaceutically acceptable salt present at a concentration ranging from about 0.7 mg/ml to about 21 mg/ml, an osmogent and an inert gas in solution in a parenteral aqueous vehicle, the solution having a volume ranging from about 50 ml to 1000 ml,
(b) a rigid infusion container containing the composition of (a) and an inert gas in the headspace,
(c) optionally, a second container surrounding the infusion container.

further wherein the intravenous infusion dosage form is sterilized by moist heat sterilization, and wherein the total impurities are less than 2.0% by weight.

Typically, the rigid infusion containers suitable for the intravenous infusion dosage form of the present invention are made up of a material such as glass, particularly, Type I siliconized glass. Non limiting examples of the rigid infusion containers include an infusion vial, an infusion bottle, or a pre-filled syringe having capacity to fill 50 ml to 1000 ml, preferably, 100 ml to 500 ml of the solution.

In one embodiment, the intravenous infusion dosage form comprises a second container. In one embodiment the second container contains the infusion container. The second container may suitably be a pouch, or bag or film or overwrap or carton that surrounds the infusion container. In one embodiment, the second containers not only provide protection to the pemetrexed solution from light, but also protects the infusion container from being tampered or misused. It is designed in a manner so as to provide unique identity to the intravenous dosage form of the present invention. The second containers are made up of a material having oxygen, light and moisture barrier properties. The second container may also be fused with the infusion container wherein there may not be a space between the two containers. The fusion of the second container with the infusion container is possible in various ways. For example, the fused container is an in-situ formed and sealed by packing the infusion container into the second container and subjecting to compression at a melting temperature. Here the infusion container is a rigid container and the material of the second container contacting the infusion container has a melting point below the melting temperature used in the process. Alternatively, a rigid infusion container can be coated with a solution or a suspension composition comprising materials having the ability to form a barrier film.

In another embodiment, the second container may be a multilayered overwrap pouch, having one layer made up of oxygen scavenging material. Non limiting example of the material constituting second containers include, aluminum, various polymers and copolymers like polyamide, ethylenevinyl alcohol copolymer etc. Aluminum based containers are preferred and include aluminium pouches, aluminium plated films, aluminium foils, aluminum laminate films, composite aluminum films co-extruded with other polymers like polyethylene, polypropylene, EVA, EMA, EAA etc. In one preferred embodiment, the second container is an overwrap pouch made up of composite polymer aluminium film having PET, Nylon-6, aluminium foil, and CPP (polypropylene/ethylene block copolymer) from outside to inside, the layers being either co-extruded and/or fixed using an adhesive with the other layer. In another preferred embodiment, the second container is an overwrap pouch made up of PET/NY/Aluminum/Oxygen absorbing layer/Polyethylene. In another preferred embodiment, the second container is an overwrap pouch made up of PET/NY/Aluminum/Oxygen absorbing layer/Polypropylene. In another preferred embodiment, the second container is an overwrap pouch made up of PET/NY/AL/OA/CPP.

The oxygen scavenger or oxygen scavenging layer material may be a suitable material capable of quickly absorbing oxygen and having good oxygen absorbing capacity and heat resistance. Non-limiting example of such oxygen scavenging materials include iron, silica, charcoal etc. Preferably the oxygen scavenging material is iron based material. In one embodiment, the oxygen scavenger may be an iron based self-reacting type or iron based water dependent type oxygen scavenger/absorber (such as those marketed under the brand of AGELESS®). In one preferred embodiment, the oxygen scavenger is made up of treated iron powder having an oxygen absorption time ranging from about 30 minutes to 48 hours; and handling time in open air at 25° C. ranging from 30 minutes to 4 hours.

In one preferred embodiment, the flexible infusion container is an infusion bag made up of a flexible plastic or polymeric material and the second container is an overwrap flexible pouch made up of aluminum which surrounds the infusion bag and the space between the infusion bag and overwrap pouch is occupied by an inert gas or vacuum. In one embodiment, the inert gas is used to flush out or replace the air between the space of the infusion bag and the second container, before further processing step, such as for example, subjecting to moist heat sterilization, particularly when the infusion bag is not impermeable and makes it somewhat permeable when heat and pressure are applied. Suitably, in one embodiment, the second container further comprises an oxygen scavenger, which may be placed in the space between the infusion container and the second container. In another preferred embodiment, the second container is a multilayered overwrap pouch, having one layer made up of oxygen scavenging material.

In one embodiment, when the infusion container is a rigid container for example, one that is made up of glass such as for example glass vial, the dosage form may optionally, comprise a second container. In one embodiment, the rigid infusion container is surrounded by a second container with an inert gas in the space between the infusion container and the second container. The second container when present, may be selected from a show box; an aluminium overwrap or transparent pouch covering and sealing the infusion container; or an overwrap aluminium or transparent pouch (second container) covering and sealing the infusion container, further wherein the space between the aluminium or transparent pouch and the infusion container is occupied with an inert gas (such as Nitrogen or Argon). The second container may further comprise an oxygen scavenger, which may be placed in the space between the infusion container and the second container.

It was found that the presence of an inert gas in the headspace of the infusion container was important for achieving adequate stability of Pemetrexed in the aqueous solution. This is particularly true because the intravenous infusion dosage form of the present invention is a ready to infuse i.e. directly infusible dosage form and has larger volume of the container having the composition of the pemetrexed filled in it. Pemetrexed is as such known to be highly susceptible to oxygen and in order to achieve stable solution, prior arts teach use of stabilizers and/or antioxidants. However, advantageously the solution composition of the present invention is stable inspite of absence of any added stabilizers such as antioxidants, amino acids, amines, complexing agents such as cyclodextrins or co-solvents such as propylene glycol. The intravenous infusion dosage form of the present invention provides the ability to avoid the use of antioxidants or preservatives. Over the entire shelf life, the inert gas level in the solution and in the headspace, as well as the sterility of the intravenous solution can be preserved. Further, most importantly, the intravenous infusion dosage form of the present invention provides a terminally sterilized product which is the irreplaceable option to achieve sterility of parenteral dosage forms.

According to one embodiment, wherein the infusion container is a flexible infusion container, the present invention provides a method for preparing the intravenous infusion dosage form comprising steps of
  a. dissolving pemetrexed or its pharmaceutically acceptable salt and an osmogent in a parenteral aqueous vehicle,
  b. filling the solution of step (a) into a flexible infusion container,
  c. sealing the filled flexible infusion container,
  d. surrounding the flexible infusion container by a second container and sealing the second container,
  e. subjecting the container of step (d) to moist heat sterilization,
  wherein in each of the above steps, low oxygen conditions are maintained in the solution and/or in the head space of the flexible infusion container and in the space between the flexible infusion container and second container.

The low oxygen conditions are maintained by means of purging the aqueous solution of pemetrexed with an inert gas like nitrogen or argon, wherein the dissolved oxygen levels are less than 1 parts per million, flushing or filling the headspace of the container with the inert gas and maintaining the inert atmosphere for a period of time ranging from 30 minutes to 4 hours, depending upon the manufacturing batch size. Further, the space between the flexible infusion container and the second container is replaced with an inert gas, by suitable techniques such as flushing the space between the two containers with an inert gas during sealing the second container or by creating vacuum in the space between the infusion container and second container and flushing an inert gas like nitrogen in the space and sealing the second container.

Alternatively, low oxygen conditions are maintained by creating and maintaining vacuum in the space between the flexible infusion container and the second container by complete suction and removal of air from the space. In one embodiment, the low oxygen condition is also maintained during autoclaving wherein during sterilization the air overpressure is maintained using an inert or compressed gas.

In one specific embodiment, wherein the infusion container is a flexible infusion container, the present invention also provides a method for preparing the intravenous infusion dosage form comprising steps of a. dissolving pemetrexed or its pharmaceutically acceptable salt and an osmogent in a parenteral aqueous vehicle,
b. filling the solution of step (a) into a flexible infusion container,
c. sealing the filled flexible infusion container,
d. surrounding the flexible infusion container by a second container and sealing the second container,
e. maintaining the container of d) in an enclosed chamber, which is optionally, filled with an inert gas or vacuum, at room temperature, for at least 12 hours;
f. subjecting the container of step (e) to moist heat sterilization, wherein in each of the above steps, low oxygen conditions are maintained in the solution and/or in the head space of the flexible infusion container and in the space between the flexible infusion container and second container.

The additional step of maintaining the dosage form for at least 24 hours prior to moist heat sterilization i.e. the step of providing a hold time to the sealed infusion container, before subjecting the infusion container to moist heat terminal sterilization, leads to improved stabilization, such that the dosage form shows improved stability. Suitably, in this embodiment, the hold time may vary from at least 1 hour to 5 days or more, preferably from about 12 hours to 72 hours, preferably from about 24 hours to 48 hours.

In one embodiment, wherein the intravenous infusion dosage form comprises a rigid infusion container, the dosage form is prepared by a method comprising the steps of:
a) dissolving pemetrexed or its pharmaceutically acceptable salt and an osmogent in a parenteral aqueous vehicle,
b) filling the solution of step (a) into an rigid infusion container,
c) half-stoppering the rigid container,
d) holding the half stoppered container in an enclosed chamber having an inert gas environment for at least 30 minutes,
e) stoppering and sealing the rigid container,
f) subjecting the container of step (e) to moist heat sterilization, wherein in each of the above steps, low oxygen conditions are maintained in the solution and/or in the head space of the rigid container.

The low oxygen conditions are maintained by suitable means as described. Preferably, the aqueous solution of pemetrexed is purged with an inert gas like nitrogen or argon so that the content of dissolved oxygen in the solution becomes less than 1 ppm (parts per million). Further, the headspace of the container, i.e. the space above the solution in the container, is replaced by an inert gas, by flushing the inert gas in the head space. In one embodiment the low oxygen condition is also maintained during autoclaving wherein during sterilization the air overpressure is maintained using an inert or compressed gas.

The intravenous infusion dosage form prepared by the above methods was found to have total impurities less than 2.0% by weight. Surprisingly, it was found that inspite of having no added stabilizers and subjecting the dosage form to terminal sterilization for eg. by moist heat sterilization at 121° C. for 15 minutes and at a reduced pressure of 3.5 Barr, the increase in total impurities of pemetrexed was less than 0.2% by weight. This was indeed a surprising finding. This indicates that the intravenous dosage form prepared according to this method withstands terminal sterilization without compromising on chemical stability.

Stability testing indicated that the intravenous infusion dosage forms of the present invention remained stable through-out the shelf life of the product such that the total impurities remained less than 2.0% by weight and the highest unknown impurity and other known impurities remained below 0.2% by weight at any given point in time during the shelf life of the product upon storage for 0-24 months at varying storage conditions—at room temperature and at refrigerated conditions. The solution composition of pemetrexed also remained physically stable, such that no precipitation or crystallization or color change took place upon storage and the value of percentage transmittance of the solution remained greater than 90%, preferably greater than 95% upon long term storage of 12-24 months at room temperature. In one embodiment the intravenous infusion dosage form has a shelf life of 12-24 months.

Particularly, in case of rigid containers, it was surprisingly observed that a dosage form prepared by a process which involves step of holding the half stoppered container in an enclosed chamber having an inert gas environment for at least 30 minutes prior to moist heat sterilization, show better and improved stability as compared to a dosage form prepared by a process which does not involve the said step of providing the hold time and wherein the stoppering and sterilization of the rigid container was carried out immediately after filling. Suitably, according to this embodiment, the hold time provided may vary from at least 30 minutes to 5 days or more, preferably from about 1 hour to 48 hours.

In some embodiments, when the dissolved oxygen levels in the aqueous solution during manufacturing was not controlled to less than 1 ppm (for instance by not purging an inert gas like Nitrogen in the aqueous solution), and instead the aqueous parenteral vehicle had a dissolved oxygen level of about 7 ppm, it was surprisingly found that inspite of high ppm levels of oxygen in the bulk, if a hold time before the sterilization step is provided (i.e. in case of rigid containers, holding the half stoppered rigid container in an enclosed chamber having an inert gas environment for at least 30 minutes; and in case of flexible infusion containers, keeping the flexible infusion container which is overwrapped with a second container and having an inert gas or vacuum in the space between the flexible container and the second container, for at least 12 hours at room temperature) the levels of total impurities and degradation impurities B and C and single highest unknown impurity remains well controlled after autoclaving or steam sterilization. Particularly, the level of degradation impurities B and C were dramatically well controlled as compared to another experiment wherein no hold time was provided before steam sterilization. In case of intravenous infusion dosage forms comprising the rigid container, the levels of impurities B and C observed after autoclaving were about three times lower when a hold time was provided as compared to when no hold time was provided. In case of intravenous infusion dosage forms comprising the flexible container, the levels of impurities B and C observed after autoclaving were about four times lower when a hold time of 24 hours was provided as compared to when no hold time was provided. Thus, it was surprisingly found that step of providing a hold time before the steam sterilization step, imparts a better stability to the intravenous infusion dosage form, and allows an assurance of stability even in case if the dissolved oxygen levels in the aqueous drug solution are not monitored or maintained at a level of below 1 ppm. This is quite surprising given the fact that pemetrexed is highly sensitive to oxygen and susceptible to oxidative and hydrolytic degradation.

According to the present invention, sterilization is achieved by moist heat sterilization or autoclaving wherein the filled and sealed container is terminally sterilized. In some embodiments, the intravenous infusion dosage form may be sterilized by other suitable techniques such as filtration sterilization, radiation sterilization and the like, which may be used concurrently with moist heat sterilization. In one embodiment, the intravenous infusion dosage form of the present invention is sterile. In one embodiment the intravenous infusion dosage form is sterilized using moist heat sterilization. In one specific embodiment, the present invention provides an intravenous dosage form wherein the sterilization is carried out by membrane filtration. The intravenous dosage form sterilized by the filtration method remained stable through-out the shelf life of the product such that the total impurities remained less than 2% by weight and the highest unknown impurity and other known impurities remained below 0.2% by weight at any given point in time during the shelf life of the product upon storage for 12-24 months.

The term 'stable' or 'stability' as used herein means that the intravenous infusion dosage form of the present invention is physically as well as chemically stable as demonstrated by compliance to acceptable specification upon storage at room temperature (about 25° C.) and at refrigerated conditions (2-8° C.) for prolonged period of time such as for at least twelve months, preferably eighteen months, more preferably twenty-four months or longer. Suitably, the composition of pemetrexed or its salt remains chemically stable when stored at room temperature (about 25° C.) and at refrigerated conditions (2-8° C.) with varying relative humidities such that the drug content or assay of pemetrexed remains within the specified limit of 95-105% by weight of the label claim; the highest unknown impurity remains within the specified limit of not more than 0.2%; the known impurities including the degradative impurities B and C, remains within the specified limit of not more than 0.2% and the total impurity remains less than 2.0%, preferably below 1.5%, at any point of time upon long term storage for at least twelve months, preferably eighteen months, more preferably twenty four months or longer.

In the context of this specification "comprising" is to be interpreted as "including". Aspects of the invention comprising certain elements are also intended to extend to alternative embodiments "consisting" or "consisting essentially" of the relevant elements. Where technically appropriate, embodiments of the invention may be combined.

The intravenous infusion dosage form of the present invention is suitable for use in the treatment of various types of cancers, particularly, non-small cell lung cancer and mesothelioma. The intravenous infusion dosage form may be used alone or in combination with other therapeutic agents such as, but not limited to, carboplatin, Vitamin $B_{12}$, folic acid, which other agents may be administered to the patient, prior to, simultaneously or after administration of the intravenous infusion dosage form of pemetrexed. In one embodiment, there is provided a kit comprising the intravenous infusion dosage form of pemetrexed of the present invention along with dosage form of Vitamin $B_{12}$ and/or Folic acid.

Embodiments are described herein as comprising certain features/elements. The disclosure also extends to separate embodiments consisting or consisting essentially of said features/elements.

Hereinafter, the invention is more specifically described by way of examples. The examples are not intended to limit the scope of the invention and are merely used as illustrations.

Example 1

The example illustrates preferred embodiments of the intravenous infusion dosage form of the present invention.

TABLE 1

Details of aqueous solution/composition of pemetrexed

| Ingredients | Concentration (% w/v) |
| --- | --- |
| Pemetrexed disodium heptahydrate eq. to Pemetrexed | 0.9 |
| Sodium Chloride | 0.9 |
| Sodium hydroxide and Hydrochloric acid | q.s. to adjust the pH at 7.2 |
| Water for Injection | q.s |

Method of preparation: Sodium chloride was dissolved in water for injection. Argon gas was purged into it to obtain dissolved oxygen level of less than 1 PPM (parts per million). Pemetrexed disodium heptahydrate was then added to the above solution and was dissolved by stirring. The pH of solution was checked and if needed was adjusted to 7.2 using sodium hydroxide/hydrochloric acid. The volume was made up with water for injection along with stirring for 5 min. The Argon gas purging was carried out continuously to maintain dissolved oxygen level of less than 1 PPM. The solution so prepared was filtered followed by filling the filtered solution in flexible infusion bag made up of an outer layer of polyamide 11, a middle tie of modified polyolefin and an inner layer of linear low density polyethylene, (Polyelite AE-1® infusion bag by Hosokawa); The infusion bag was then stoppered and/or sealed under inert gas environment such that the headspace is occupied by the inert gas.

The filled infusion bags were placed in a second container i.e. an aluminum overwrap pouch. The space between the infusion bag and the second container was replaced with nitrogen. The filled infusion bags surrounded by inert atmosphere within the second container were then subjected to moist heat sterilization by carrying out autoclaving at 121° C. for 8-15 min Subsequent to autoclaving, the second container i.e. the aluminum overwrap was replaced with a fresh aluminum overwrap and the space between the infusion bag and the second container was replaced with an inert gas (nitrogen). In one experiment, an oxygen scavenger was placed in the space between the infusion bag and the aluminum pouch before sealing the aluminum pouch.

The sealed kit having the infusion and second container comprising the composition or aqueous solution of pemetrexed was subjected to storage stability testing at varying storage conditions, namely at room temperature (25° C., 40% relative humidity), at refrigerated conditions (temperature 2-8° C.) and accelerated conditions (40° C./25% relative humidity). The assay of drug as well as contents of known and unknown impurities were analysed at different time points upon storage. The content of total impurities and other/related impurities were analysed by HPLC or high performance liquid chromatography method. The HPLC method used acetonitrile-ammonium formate buffer mobile phase and C-8 ((150×4.6) mm, 3.5μ) chromatographic column. The chromatograms were recorded using UV spectroscopy. The stability data upon storage at varying storage conditions and at various time points is presented below in Table 2:

terminal sterilization, i.e. moist heat sterilization in an autoclave at 121° C. for 15 minutes. The sealed vial comprising the aqueous solution of pemetrexed was subjected to

TABLE 2

Stability study results:

| Storage conditions | Time point (Months) | Assay of Pemetrexed (%) | % Impurity B | % Impurity C | % Highest unknown impurity | % Total Impurity | % Transmittance at 650 nm |
|---|---|---|---|---|---|---|---|
| Initial | 0 | 99.89 | 0.052 | 0.072 | 0.034 | 0.360 | 98.80 |
| 2-8° C. | 12 | 100.04 | 0.077 | 0.090 | 0.032 | 0.440 | 96.72 |
| 25° C./40% RH | 12 | 99.92 | 0.125 | 0.141 | 0.041 | 0.599 | 95.50 |
| 40° C./75% RH | 6 | 101.38 | 0.051 | 0.056 | 0.029 | 0.498 | 98.32 |

It was observed that the intravenous infusion dosage form show long term stability upon storage. The increase in total impurities of pemetrexed during moist heat sterilization remained less than 0.2%. {The value of total impurities measured before performing the step of terminal sterilization was 0.307%, which marginally varied to 0.36% after moist heat sterilization}. The total impurities remained less than 1.0% by weight upon storage for 12 months and the highest unknown impurity and other known impurities remained below 0.2% by weight. The assay value of Pemetrexed remained almost unchanged upon storage wherein the values are maintained well within the range of 95%-105%. Further, it was observed that the aqueous solution of pemetrexed remained physically stable, such that no precipitation or crystallization or color change take place upon storage and the value of percentage transmittance of the solution remained greater than 90%, preferably greater than 95% upon long term storage of 12-24 months at room temperature. Surprisingly, the composition of pemetrexed also remained chemically stable upon storage at accelerated stability testing condition of 40° C., 25% relative humidity for a period of 6 months, which correlated to room temperature shelf life stability for 24 months. The intravenous infusion dosage form thus remains stable for the shelf life of the product.

Further experiments similar to the one described above were performed by using different flexible containers i.e. (a) infusion bags supplied by Hosokawa under the brand Polyelite EHC® film bag, (b) infusion bags supplied by Technoflex under the brand Inerta 103® (c) infusion bags supplied by Sealer Air Corporation under the brand—M312 and M312A® films. Storage stability studies at various conditions as described in previous experiment were carried out and it was observed that the intravenous infusion dosage forms were stable for the shelf life of the product. In all cases, the total impurities remained less than 1.0% by weight upon storage for 12 months and the highest unknown impurity and other known impurities remained below 0.2% by weight.

In another experiment, the bulk solution of pemetrexed so prepared after filtration, was aseptically filled in a rigid container, i.e. a glass vial. The filling was accompanied by flushing of the vial headspace with an inert gas and the processing was done under inert gas environment. The vials were half stoppered using sterile dried rubber stoppers. The half stoppered vials were loaded into an enclosed chamber having an inert atmosphere and was kept there on hold for time period of at least 30 minutes, followed by replacing the inert gas in the environment with fresh pure inert gas and then full stoppering of the vials. The stoppered vials were then sealed with flip off and subsequently subjected to storage stability testing at varying storage conditions, namely at room temperature (25° C., 60% relative humidity), at refrigerated conditions (temperature 2-8° C.) and accelerated conditions (40° C./75% relative humidity). The drug content as well as contents of known and unknown impurities were analysed at different time points upon storage using the HPLC method described above.

It was observed that the intravenous infusion dosage form show long term stability upon storage. The increase in total impurities of pemetrexed during moist heat sterilization remained less than 0.2%. The total impurities remained less than 2% by weight and the highest unknown impurity and other known impurities remained below 0.2% by weight upon storage for 24 months. The assay value of Pemetrexed remained almost unchanged upon storage wherein the values are maintained well within the range of 95%-105%. Further, it was observed that the aqueous solution of pemetrexed remained physically stable, such that no precipitation or crystallization or color change take place upon storage and the value of percentage transmittance of the solution remained greater than 90%, preferably greater than 95% upon long term storage for 24 months at room temperature and at refrigerated conditions. The composition of pemetrexed also remained chemically stable upon storage at accelerated stability testing condition of 40° C., 75% relative humidity for a period of 6 months, which correlated to room temperature shelf life stability for 24 months.

Comparative Examples 1 and 2

Pemetrexed solution was prepared according to Example 1 and filled into a flexible infusion container. The infusion container was sealed as given in Example 1.

In the comparative Example 1, the filled infusion container was not covered with a second container.

In comparative example 2, the filled and sealed infusion container was packed in the second container. The space between the infusion container and the second container was filled with air instead of inert gas or vacuum. In both the examples, the filled and sealed infusion containers were subjected to moist heat sterilization in an autoclave at 121° C., 3.5 Barr pressure, for 15 minutes.

It was observed that the dosage form prepared according to comparative example 1 and comparative example 2, were not stable. High levels of impurities were formed immediately after moist heat sterilization as well as on storage. Particularly in comparative example 2, the levels of total impurities, the level of Impurity A and Impurity B, analyzed just after autoclaving as well as upon storage on shelf, were found to be significantly higher compared to the dosage form in which the flexible infusion container was overwrapped with a second container along with an inert gas in between the flexible container and the second container. In the comparative example 2, the level of impurities A and B crossed the limit of 0.2% just after autoclaving and when containers filled with the sterile solution were subjected to storage stability under accelerated conditions at 40° C., the stability results indicated that the drug solution upon storage was unstable, and the assay of pemetrexed dropped down drastically from initial 99.5% to about 69% after 1 month storage.

The invention claimed is:

1. An intravenous infusion dosage form comprising:
   a) an aqueous composition comprising about 0.7 mg/ml to about 21 mg/ml of pemetrexed or its pharmaceutically acceptable salt, and an osmogent; and
   b) a flexible infusion container containing the aqueous composition in a volume ranging from about 50 ml to about 1000 ml:
   wherein the dosage form has less than 0.5% by weight of individual impurity B or impurity C after storage at 15-30° C. for at least 12 months, and
   the aqueous composition is free of antioxidants.

2. The intravenous infusion dosage form of claim 1, wherein the dosage form is subjected to moist heat sterilization.

3. The intravenous infusion dosage form of claim 1, wherein the container comprises a headspace, wherein the headspace is optionally occupied with an inert gas.

4. The intravenous infusion dosage form of claim 1, wherein the dosage form comprises a second container surrounding the flexible infusion container, and the dosage form has a space between the second container and the flexible infusion container.

5. The intravenous infusion dosage form of claim 4, wherein the second container is a flexible container or a solid container.

6. The intravenous infusion dosage form of claim 4, wherein the space between the two containers optionally has an inert gas or oxygen scavenger.

7. The intravenous infusion dosage form of claim 1, wherein the level of total impurities is less than 2.0% by weight after storage at 15-30° C. for at least 12 months.

8. The intravenous infusion dosage form of claim 1, wherein the oxygen content in the dosage form is maintained below 2 ppm for at least 12 months.

9. The intravenous infusion dosage form of claim 8, wherein the oxygen content is maintained by inert gas purging and/or filling.

10. The intravenous infusion dosage form of claim 4, wherein the second container is made of aluminum.

11. The intravenous infusion dosage of claim 6, wherein the inert gas is selected from nitrogen, argon and helium.

12. A method of treating cancer in a patient in need thereof, the method comprising administering an intravenous infusion dosage form to the patient, wherein the intravenous infusion dosage comprises:
   a) an aqueous composition comprising about 0.7 mg/ml to about 21 mg/ml of pemetrexed or its pharmaceutically acceptable salt, and an osmogent; and
   b) a flexible infusion container containing the composition in a volume ranging from about 50 ml to about 1000 ml;
   wherein the dosage form has less than 0.5% by weight of individual impurity B or impurity C after storage at 15-30° C. for at least 12 months, and
   the aqueous composition is free of antioxidants.

13. The method of claim 12, wherein the cancer is selected from lung cancer, breast cancer, cervical cancer, colorectal cancer, cutaneous squamous cell carcinoma, endometrial carcinoma, esophageal cancer, gastric cancer, head and neck cancer, squamous cell cancer, hepatocellular carcinoma, Hodgkin lymphoma, malignant pleural mesothelioma, melanoma, Merkel cell carcinoma, microsatellite instability-high or mismatch repair-deficient cancer (unresectable or metastatic), non-small cell lung cancer, primary mediastinal large B-cell lymphoma, renal cell carcinoma, small cell lung cancer, and urothelial carcinoma.

14. The method of claim 13, wherein the lung cancer is small cell or non-small cell lung cancer.

15. An intravenous infusion dosage form comprising:
   a) an aqueous composition consisting essentially of about 0.7 mg/ml to about 21 mg/ml of pemetrexed or its pharmaceutically acceptable salt, and an osmogent; and
   b) a flexible infusion container containing the aqueous composition in a volume ranging from about 50 ml to about 1000 ml:
   wherein the dosage form has less than 0.5% by weight of individual impurity B or impurity C after storage at 15-30° C. for at least 12 months.

16. The intravenous infusion dosage form of claim 1, wherein the dosage form is a ready to use infusion dosage form.

* * * * *